United States Patent

Yoshioka et al.

[11] Patent Number: 4,612,372
[45] Date of Patent: Sep. 16, 1986

[54] TYLOSIN DERIVATIVES

[75] Inventors: Takeo Yoshioka, Ayase; Miharu Maeda, Yokohama; Rokuro Okamoto, Fujisawa; Yasutaka Shimauchi, Ninomiya; Tomoyuki Ishikura, Chigasaki; Tsutomu Sawa, Ayase; Tomio Takeuchi; Hamao Umezawa, both of Tokyo, all of Japan

[73] Assignee: Sanraku Incorporated, Tokyo, Japan

[21] Appl. No.: 754,568

[22] Filed: Jul. 12, 1985

[30] Foreign Application Priority Data

Jul. 20, 1984 [JP] Japan .................................. 59-151884
Dec. 10, 1984 [JP] Japan .................................. 59-261536

[51] Int. Cl.$^4$ ............................................ C07H 17/08
[52] U.S. Cl. .................................................... 536/7.1
[58] Field of Search .......................................... 536/7.1

[56] References Cited

U.S. PATENT DOCUMENTS 4,205,163  5/1980  Mori et al. .......................... 536/7.1

FOREIGN PATENT DOCUMENTS 0052361  5/1982  European Pat. Off. ............. 536/7.1

Primary Examiner—Johnnie R. Brown
Assistant Examiner—Elli Peselev
Attorney, Agent, or Firm—Frank J. Jordan; C. Bruce Hamburg; Manabu Kanesaka

[57] ABSTRACT

Novel tylosin derivatives are represented by formula:

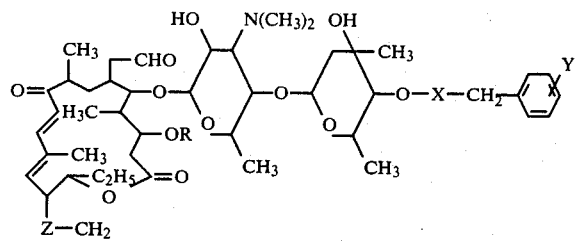

wherein R represents a hydrogen atom, an acetyl group or a propionyl group; X represents a group —CO— or —SO$_2$—; Y represents a fluorine atom, an acetyl group, a methanesulfonyl group, a methylthio group, a benzoyl group or a methoxy group bound to the benzyl group at the 2-position or 4-position; and Z represents a hydrogen atom or a D-mycinose residue:

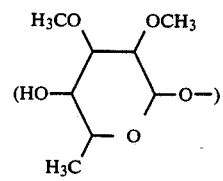

The tylosin derivatives which are antibiotics of macrolide type provide improved antibacterial activity and improved ability of absorption and excretion in vivo.

4 Claims, No Drawings

TYLOSIN DERIVATIVES

BACKGROUND OF THE INVENTION

1. Field of the Invention

The present invention relates to novel tylosin derivatives which are macrolide antibiotics and more particularly, to novel tylosin derivatives which are chemically produced.

2. Description of the Prior Art

Tylosin is classified into the oldest class of macrolide antibiotics and has been widely used as agents for treating infectious diseases of animals and as feed additives. In recent years, a variety of derivatives have been proposed by chemical or biological conversion, with attempts to enhance its antibacterial activity and at the same time, improve its ability of absorption and excretion in vivo.

As those obtained by the chemical conversion, there are various acyl derivatives of the 4"-hydroxyl group on tylosin, for example, those described in U.S. Pat. No. 4,205,163, etc.; and there are those described in, for example, U.S. Pat. No. 4,092,473, etc. as the derivatives obtained by the biological conversion.

These known tylosin derivatives described above all exhibit improved antibacterial activity against various pathogenic organisms in in vivo test and an enhanced ability of absorption and excretion of the medicament in vivo, as compared to tylosin.

However, these derivatives involved drawbacts as medicaments for treating infectious diseases because derivatives having a high antibacterial activity have poor stability in vivo (for example, they are readily decomposed by liver homogenate of mammals, etc.), or conversely, those having an improved in vivo stability show only poor antibacterial activity against drug-resistant bacteria in specific clinical fields, or the like.

SUMMARY OF THE INVENTION

The present invention provides novel tylosin derivatives represented by formula:

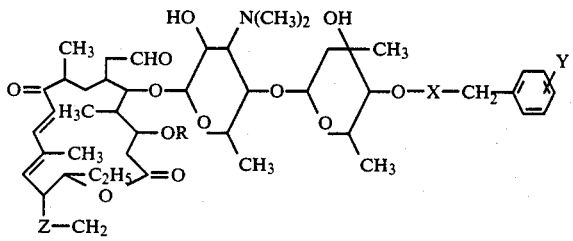

wherein R represents a hydrogen atom, an acetyl group or a propionyl group; X represents a group —CO— or —SO$_2$—; Y represents a fluorine atom, an acetyl group, a methanesulfonyl group, a methylthio group, a benzoyl group or a methoxy group bound to the benzyl group at the 2-position or 4-position; and Z represents a hydrogen atom or a D-mycinose residue:

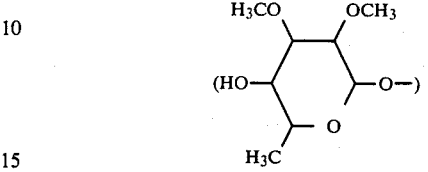

The tylosin derivatives exhibit a potent antibacterial activity against drug-resistant bacteria and at the same time, are stable against decomposition with mouse liver homogenate.

DETAILED DESCRIPTION OF THE PREFERRED EMBODIMENT

The present invention provides novel tylosin derivatives represented by formula:

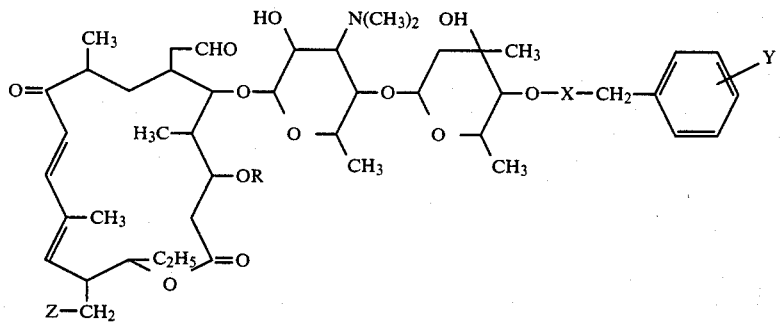

wherein R represents a hydrogen atom, an acetyl group or a propionyl group; X represents a group —CO— or —SO$_2$—; Y represents a fluorine atom, an acetyl group, a methanesulfonyl group, a methylthio group, a benzoyl group or a methoxy group bound to the benzyl group at the 2-position or 4-position; and Z represents a hydrogen atom or a D-mycinose residue:

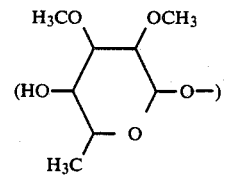

Specific examples of these derivatives include:
4"-O-(4-methanesulfonylphenylacetyl)tylosin
3-O-Acetyl-4"-O-(4-methanesulfonylphenylacetyl)tylosin
3-O-Propionyl-4"-O-(4-methanesulfonylphenylacetyl)tylosin
4"-O-(2-Methanesulfonylphenylacetyl)tylosin
3-O-Acetyl-4"-O-(4-methoxyphenylacetyl)tylosin
3-O-Propionyl-4"-O-(4-methoxyphenylacetyl)tylosin
4"O-(2-Methoxyphenylacetyl)tylosin
3-O-Acetyl-4"-O-(4-methylthiophenylacetyl)tylosin
3-O-Propionyl-4"-O-(4-methylthiophenylacetyl)tylosin 3-O-Acetyl-4"-O-(2-methylthiophenylacetyl)tylosin
3-O-Acetyl-4"-O-(4-benzoylphenylacetyl)tylosin
4"-O-(2-Benzoylphenylacetyl)tylosin
4"-O-(4-Benzoylphenylacetyl)-23-demycinosiloxytylosin
4"-O-(4-Acetylphenylacetyl)-23-demycinosiloxytylosin
4"-O-(4-Fluorophenylacetyl)tylosin
4"-O-(4-Fluorobenzylsulfonyl)tylosin
4"-O-(4-Acetylphenylacetyl)tylosin
4"-O-(2-Fluorophenylacetyl)tylosin
3-O-Acetyl-4"-O-(4-acetylphenylacetyl)tylosin Of these derivatives described above, those having a nuclear substituent of the 4"-O-phenylacetyl group or benzylsulfonyl group of tylosin bound to the 4-position of the phenyl group are particularly preferred because of the antibacterial activity against drug-resistant bacteria and the stability against decomposition with liver homogenate of mammals.

These derivatives all show a potent antibacterial activity against pathogenic microorganisms such as various Gram-positive bacteria, Gram-negative bacteria, mycoplasma, etc. In particular, these derivatives not only exhibit the activity against the drug-resistant bacteria to *Staphylococcus aureus* equivalent to the activity against sensitive bacteria but also are stable to the decomposition by liver homogenate of mice. Therefore, the derivatives are useful as medicaments, animal drugs, feed additives, etc.

The activity is shown by the following test.

ANTIBACTERIAL ACTIVITY

The antibacterial activity was determined by a tube dilution method using plain heart infusion broth (pH 7.5) as medium. The results are shown in Table 1 below.

TABLE 1

Antibacterial Activity (Minimum Inhibitory Concentration) λ/ml

| Specimen | 1 | | 2 | | 3 | | 4 | | 5 | | Control 1 | |
|---|---|---|---|---|---|---|---|---|---|---|---|---|
| 4''-O-Substituent | C(=O)-CH₂-C₆H₄-S(=O)(=O)-CH₃ | | C(=O)-CH₂-C₆H₄-SCH₃ | | C(=O)-CH₃ | | C(=O)-C₆H₅ | | C(=O)-CH₂-C₆H₄-OCH₃ | | C(=O)-CH₂-C₆H₅ | |
| 3-O-Substituent | H | | H | | H | | H | | H | | H | |
| 2-3-Substituent | mycinose | | mycinose | | H | | mycinose | | mycinose | | mycinose | |
| Bacteria Tested | | | | | | | | | | | | |
| Staphylococcus aureus 193 | 1.56 | | 1.56 | | 0.39 | | 0.78 | | 0.39 | | | |
| Staphylococcus aureus EMF | 1.56 | | 1.56 | | 0.39 | | 0.78 | | 0.78 | | | |
| Staphylococcus aureus 209P | 1.56 | | 0.78 | | 0.39 | | 1.56 | | 0.78 | | 0.78 | |
| Staphylococcus aureus MS 8710 | 6.25 | | 6.25 | | 100 | | 6.25 | | 6.25 | | 50 | |
| Staphylococcus aureus MS 9351 | 6.25 | | 6.25 | | 100 | | 6.25 | | 3.12 | | | |
| Staphylococcus aureus MS 9610 | 6.25 | | 3.12 | | 100 | | 6.25 | | 3.12 | | >100 | |
| Staphylococcus aureus MS 9861 | 0.78 | | 3.12 | | 1.56 | | 3.12 | | 1.56 | | | |
| Staphylococcus aureus MS 9937 | 1.56 | | 0.78 | | 6.25 | | 3.12 | | 3.12 | | | |
| Staphylococcus aureus MS 10225 | 0.78 | | 6.25 | | 0.39 | | 1.56 | | 0.78 | | | |
| Staphylococcus aureus MS 10246 | 6.25 | | 3.12 | | 100 | | 6.25 | | 6.25 | | | |
| Staphylococcus aureus Smith | 1.56 | | 3.12 | | 1.56 | | 3.12 | | 3.12 | | | |
| Micrococcus luteus PCI 1001 | 0.39 | | 0.39 | | 0.39 | | 0.78 | | 0.39 | | | |
| Bacillus subtilis MRRL B-558 | 1.56 | | 1.56 | | 0.78 | | 3.12 | | 1.56 | | | |
| Corynebacterium bovis 1810 | 0.39 | | 0.39 | | 0.39 | | 0.78 | | 0.39 | | | |
| Escherichia coli NIHJ | 100 | | 50 | | 25 | | >100 | | 50 | | | |
| Klebsiella Pneumoniae PCI 602 | 25 | | 12.5 | | 6.25 | | 12.5 | | 6.25 | | | |
| Shigella dysenteriae JS 11910 | 6.25 | | 6.25 | | 3.12 | | 12.5 | | 6.25 | | | |
| Salmonella enteritidis 1891 | 25 | | 25 | | 12.5 | | >100 | | 50 | | | |
| Serratia marcescens | 100 | | 50 | | 100 | | 100 | | 100 | | | |
| Pseudomonas aeruginosa A3 | >100 >100 | | >100 | | >100 | | | | | | | |

TABLE 1-continued

Antibacterial Activity (Minimum Inhibitory Concentration) λ/ml

| Specimen | Control 2 | | | 6 | | | 7 | | | 8 | | | 9 | | | 10 | | | Control 3 | | | Control 4 | | |
|---|---|---|---|---|---|---|---|---|---|---|---|---|---|---|---|---|---|---|---|---|---|---|---|---|
| 4″-O—Substituent | C—CH₂—S—⌬ / O=  (with F) | | | C—CH₂—⌬—F / C=O | | | O=S=O / CH₂—⌬—F | | | C—CH₂—⌬ / C=O | | | C—CH₂—⌬ (F) / C=O | | | C—CH₂—⌬—C(=O)CH₃ / C=O | | | C—CH₂—⌬ / C=O | | | CH₂—⌬ / O=S=O | | |
| 3-O—Substituent | H | | | H | | | H | | | H | | | H | | | H | | | H | | | H | | |
| 2-3-Substituent | mycinose | | | mycinose | | | mycinose | | | mycinose | | | mycinose | | | mycinose | | | mycinose | | | mycinose | | |
| Compound No. | | | | 6 | | | 7 | | | 8 | | | 9 | | | 10 | | | | | | | | |
| Bacteria Tested | | | | | | | | | | | | | | | | | | | | | | | | |
| Staphylococcus aureus 193 | 0.78 | | | 0.78 | | | 0.39 | | | 0.78 | | | 1.56 | | | 0.78 | | | | | | | | |
| Staphylococcus aureus EMF | 0.78 | | | 0.78 | | | 0.78 | | | 0.78 | | | 1.56 | | | 0.78 | | | | | | | | |
| Staphylococcus aureus 209P | 0.78 | | | 0.78 | | | 0.39 | | | 0.39 | | | 0.78 | | | 0.39 | | | 0.78 | | | 0.78 | | |
| Staphylococcus aureus MS 8710 | 6.25 | | | 6.25 | | | 6.25 | | | 3.12 | | | 12.5 | | | 3.12 | | | 50 | | | 25 | | |
| Staphylococcus aureus MS 9351 | 6.25 | | | 3.12 | | | 6.25 | | | 3.12 | | | 3.12 | | | 3.12 | | | | | | | | |
| Staphylococcus aureus MS 9610 | 6.25 | | | 6.25 | | | 6.25 | | | 3.12 | | | 12.5 | | | 3.12 | | | >100 | | | >100 | | |
| Staphylococcus aureus MS 9861 | 1.56 | | | 1.56 | | | 1.56 | | | 1.56 | | | 3.12 | | | 1.56 | | | | | | | | |
| Staphylococcus aureus MS 9937 | 1.56 | | | 1.56 | | | 1.56 | | | 3.12 | | | 1.56 | | | 3.12 | | | | | | | | |
| Staphylococcus aureus MS 10225 | 1.56 | | | 0.78 | | | 0.78 | | | 0.78 | | | 1.56 | | | 0.78 | | | | | | | | |
| Staphylococcus aureus MS 10246 | 12.5 | | | 3.12 | | | 12.5 | | | 6.25 | | | 12.5 | | | 6.25 | | | | | | | | |
| Staphylococcus aureus Smith | 1.56 | | | 1.56 | | | 1.56 | | | 3.12 | | | 1.56 | | | 3.12 | | | | | | | | |
| Micrococcus luteus PCI 1001 | <0.2 | | | <0.2 | | | <0.2 | | | <0.2 | | | <0.2 | | | <0.2 | | | | | | | | |
| Bacillus subtilis B-558 | 1.56 | | | 0.39 | | | 0.78 | | | 0.78 | | | 1.56 | | | 0.78 | | | | | | | | |
| Corynebacterium bovis 1810 | 0.39 | | | <0.2 | | | <0.2 | | | 0.39 | | | <0.2 | | | 0.39 | | | | | | | | |
| Escherichia coli NIHJ | 50 | | | 50 | | | 50 | | | 100 | | | 50 | | | 100 | | | | | | | | |
| Klebsiella Pheumoniae PCI 602 | 12.5 | | | 3.12 | | | 12.5 | | | 12.5 | | | 12.5 | | | 12.5 | | | | | | | | |
| Shigella dysenteriae JS 11910 | 6.25 | | | 1.56 | | | 3.12 | | | 6.25 | | | 6.25 | | | 6.25 | | | | | | | | |
| Salmonella enteritidis 1891 | 25 | | | 12.5 | | | 12.5 | | | 25 | | | 25 | | | 25 | | | | | | | | |
| Serratia marcescens | 50 | | | 50 | | | 50 | | | 100 | | | 50 | | | 100 | | | | | | | | |
| Pseudomonas aeruginosa | 100 | | | 100 | | | 50 | | | 100 | | | 100 | | | 100 | | | | | | | | |

TEST ON STABILITY AGAINST LIVER HOMOGENATE OF MICE

Liver from ICB strain mice was homogenated with a potter's homogenizer (3000 rpm, 10 minutes) together with a 5-fold amount of 0.1M phosphate buffer (pH 7.2). To the supernatant was added 1 ml of a 500 μg/ml (10% methanolic water) of a specimen. After the mixture was reacted at 37° C. for 1 hour, the reaction mixture was heated at 100° C. for 3 minutes. Then, 1 ml of 0.1M phosphate buffer (pH 9.0) was added thereto and extracted with 1 ml of ethyl acetate. The organic layer was subjected to silica gel thin layer chromatograph y (chloroform/methanol/ammonia=15/1.2/0.1). By a chromatographic scanner (283 nm), a formation ratio of the unchanged substance to the hydrolysate was determined and the formation of the hydrolysate was expressed by percentage. The results are shown in Table 2.

TABLE 2

| | Stability to Liver Homogenate of Mice | | | | | | | | | | | | |
|---|---|---|---|---|---|---|---|---|---|---|---|---|---|
| | Specimen (Compound No.) | | | | | | | | | | Control | | |
| | 1 | 2 | 3 | 4 | 5 | 6 | 7 | 8 | 9 | 10 | 2 | 3 | 4 |
| Residual Intact Compound Rate* (%) | 89 | 84 | 95 | 82 | 94 | 95 | <95 | <95 | 95 | <95 | 0 | <95 | 0 |

*Time of contact with homogenate: 60 minutes

From the above results, it is apparent that the compounds of the present invention show a high antibacterial activity against macrolide-sensitive bacteria and the resistant bacteria and further exhibit high stability in the hydrolysis test using liver homogenate of the mammal. Therefore, these compounds can be excellent drugs for treating infections diseases.

According to proposal previously made by the present inventors (for example, U.S. Pat. No. 4,205,163), 4"-O-phenylthioacetyltylosin (control compound 2) is the most effective tylosin derivative against macrolide-resistant bacteria. However, this derivative provides merely unsatisfactory results in an experiment of treatment for infectious diseases of mice, since the 4"-O-phenylacetyl group is completely hydrolyzed by esterase in vivl (particularly in liver) although the derivative shows a high antibacterial activity in vitro. On the other hand, it is suggested that 4"-O-phenylacetyl derivative (control compound 1) showing a good result in the foregoing stability test using liver homogenate would generally be poor in antibacterial activity against resistant bacteria.

The compounds of the present invention represented by the foregoing formula (I) can be produced by protecting a hydroxy group(s) of tylosin or 3-O-acyltylosin (cf. Published Examined Japanese Patent Application 13711/78, etc.) or demycinosiloxytylosin (hereinafter referred to as YT3927; cf. E.P.O. Publication No. 52,361, etc.) used as starting materials at the 3- and/or 2'-position(s) and, if necessary, further at the 4'''-position, acylating the 4"-O-position with a desired acylating agent; and then splitting the protective group(s) at the 3- and/or 2'-position and, if necessary, further at the 4'''-position through partial hydrolysis.

More advantageously, the compounds of the present invention can be produced by selectively acetylating the hydroxy group of tylosin or YT3927 at the 2'-position (2-position of mycaminose) using acetyl chloride or acetic anhydride, etc.; reacting the acetylated product with a reactive derivative of an acid shown by formula below:

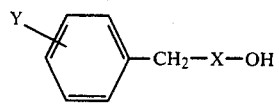

wherein X and Y have the same significances as defined above, to introduce group:

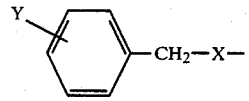

into 2'-O-acetyltylosin at the 4"-O- and 4'''-O-positions or into 2'-O-acetyl YT 3927 at the 4"-O-position; and then selectively splitting off the substituents at the 2'-O- and 4'''-O-positions.

The reaction for introducing the group:

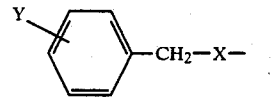

can be performed by conventional acylation. For example, the reaction may be carried out generally at temperatures from −30° C. to a reflux temperature of the reaction mixture, preferably at temperatures of −20° to 60° C. in the absence of any solvent or using an appropriate inert solvent, for example, methylene chloride, chloroform, ethyl acetate, acetone, benzene, toluene, tetrahydrofuran, acetonitrile, etc. In this case, when tylosin is used as a starting material, it is preferred that the reaction be carried out at temperatures lower than room temperature in order to avoid by-production of the O-acylated product of tylosin at the 3-position.

As the reactive derivatives of acids shown by formula (II) used as acylating agents in the aforesaid reaction, there are halides (particularly chlorides), acid anhydrides or mixed acid anhydrides (for example, an anhydride of the acid of formula (II) and pivalic acid). The amount of such reactive derivatives of acids to be used is not strictly limited but they can be used generally in an amount of 1 to 50 mols, preferably 2 to 30 mols per 1 mol of 2'-O-acetyltylosin or 2'-O-acetyl YT 3927.

Further, the acylation described above may be carried out, if necessary, in the presence of an acid binding agent. Examples of the acid binding agents which can be used include organic bases such as pyridine, cholidine, N-methylpiperidine, triethylamine, dimethylaniline, etc. The base is used generally in an amount of 2 to 50 equivalents, preferably 2 to 30 equivalents, per 1 mol of 2'-O-acetyltylosin or 2'-O-acetyl YT 3927. However, in the case of liquid bases such as pyridine, etc., these bases can be substituted for the solvent, by the use of the bases in a large excess amount.

Thus, compounds wherein group:

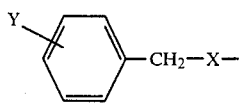

is introduced at the 4″-O- and 4‴-O-positions of 2′-O-acetyltylosin or at the 4″-O-position of 2′-O-acetyl YT 3927 can be produced.

The compounds can be separated from the reaction mixture in a conventional manner and are further subjected to partial hydrolysis shown below, after of without separation. Namely, the selecting removal of the acyl group(s) of the compounds at the 2′-O- and/or 4‴-O-position(s) can be performed as follows: after the compounds are dissolved or suspended in organic solvents which are compatible with water and dissolve the compounds, if necessary, by adding water to the solvents, the acetyl group at the 2′-O-position is previously split off under reflux, the reaction solution is allowed to cool, if necessary, and then, the reaction solution is treated with a base by adding the base thereto, whereby the acyl group at the 4‴-O-position. Preferred examples of the organic solvents used in this reaction include lower alkanols such as methanol, ethanol, etc.; ethers such as tetrahydrofuran, dioxane, etc.

Further, as bases which are added after the reaction solution is allowed to cool, there can be used ammonia, methyl amine, dimethyl amine, etc. The addition amount of these bases varies depending upon kind of base employed but not critical. However, it is advantageous from viewpoints of selectivity of splitting off reaction and reaction procedures that the concentration of the base be set forth in a range of 1 to 10 wt%. The reaction for splitting of the acyl group at the 4‴-O-position can be carried out at temperatures of −10° to 40° C., preferably 0° to 5° C., for about 1 to 48 hours, while stirring. The thus produced derivatives shown by formula (I) of the present invention can be isolated and purified from the reaction solution by means of various conventional chromatography treatments, etc.

Hereafter the present invention will be described in more detail, referring to the examples below.

In the Examples, the macrocyclic lactolone moiety of tylosin shown by formula:

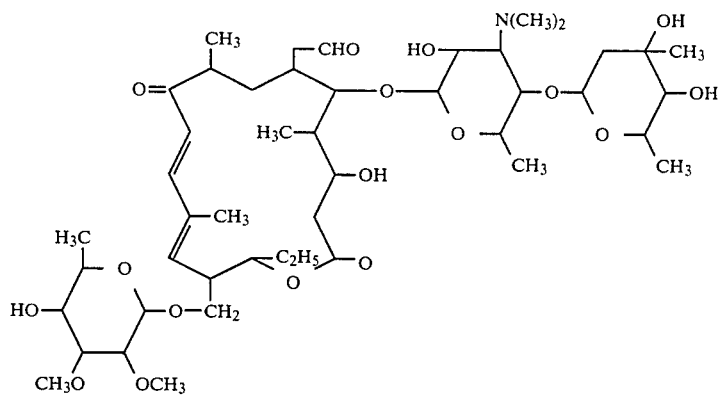

is simply referred to as:

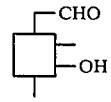

EXAMPLE 1

Preparation of 4″-O-(4-Methylsulfonylphenylacetyl)tylosin (1) 2′-O-Acetyl-4‴-O-chloroacetyl-4″-O-(4-methylsulfonylphenylacetyl)tylosin:

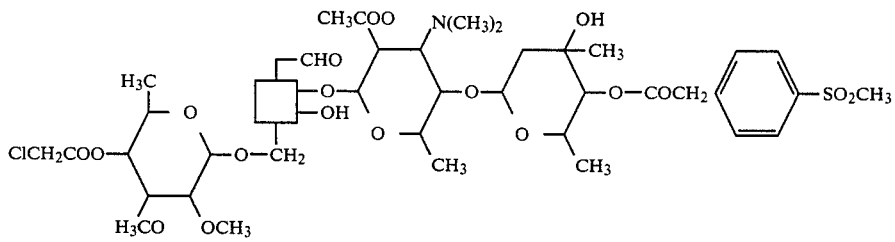

In 5 ml of ethyl acetate and 0.33 ml (2.3 mmols) of triethyl amine was dissolved 500 mg (2.3 mmols) of p-methylsulfonylphenylacetic acid. Under cooling to −15° C., 0.29 ml (2.3 mmols) of pivalic chloride was added to the solution followed by stirring for 20 minutes. The temperature was elevated to 0° C. To the mixture were added 0.8 ml (10 mmols) of pyridine and 1.2 g (1.16 mmol) of 2′-O-acetyl-4‴-O-chloroacetyltylosin. The mixture was stirred for 2 hours. A sodium hydrogen carbonate aqueous solution and 1 ml of methanol were added to the reaction solution. After stirring the mixture for 20 minutes, the organic layer was separated and washed with an aqueous sodium chloride solution. After drying over sodium sulfate, the organic layer was concentrated under reduced pressure. Toluene was added to the residue. The mixture was again concentrated under reduced pressure to remove pyridine. The residue was subjected to column chromatography (developing solvent: benzene/acetone (5/1)) using 40 g of silica gel. The fractions eluted out in TLC using silica gel developed with benzene/acetone (2/1) which exhibited a color with sulfuric acid at an RF value of 0.50 were collected and concentrated under reduced pressure to obtain 1.1 g of the above-mentioned compound. Yield 80%.

NMR (CDCl$_3$): Major peaks are shown below:

| δ(ppm) | | | |
|---|---|---|---|
| 9.59 | 1H | s | CHO |
| 7.81 | 2H | d | J = 8 Hz, 4″′-OCOCH$_2$-C$_6$H$_4$-SO$_2$CH$_3$ |
| 7.44 | 2H | d | J = 8 Hz, 4″′-OCOCH$_2$-C$_6$H$_4$-SO$_2$CH$_3$ |
| 7.25 | 1H | d | J = 16 Hz  H$_{11}$ |
| 6.21 | 1H | d | J = 16 Hz  H$_{10}$ |
| 5.84 | 1H | d | J = 10 Hz  H$_{13}$ |
| 4.05 | 2H | s | 4″′-OCOCH$_2$Cl |
| 3.78 | 2H | s | 4″-OCOCH$_2$-C$_6$H$_4$-SO$_2$CH$_3$ |
| 3.49 | 3H | s | 3″′-OCH$_3$ |
| 3.44 | 3H | s | 2″′-OCH$_3$ |
| 3.00 | 3H | s | 4″-OCOCH$_2$-C$_6$H$_4$-SO$_2$CH$_3$ |
| 2.35 | 6H | s | 3′-N(CH$_3$)$_2$ |
| 2.04 | 3H | s | 2′-OCOCH$_3$ |
| 1.76 | 3H | s | 12-CH$_3$ |

(2) 4″-O-(4-Methylsulfonylphenylacetyl)tylosin:

to column chromatography (developing solvent: benzene/acetone (3/1)) using 25 g of silica gel. The fractions eluted out in TLC using silica gel developed with benzene/acetone (3/2) which exhibited a color with sulfuric acid at an Rf value of 0.23 were collected and concentrated under reduced pressure. The residual white powders were washed with 2 ml of isopropyl ether to obtain 730 mg of the above-mentioned compound. Yield 71%.

m.p.: 121°–126° C.

$[\alpha]_D$: −40.7° (c 1.0, CH$_3$OH). UV: $\lambda_{max}^{CH3OH}$ 283.5 nm (ε 20000), 223.5 nm (ε 14000).

IR: $\nu_{max}^{KBr}$ cm$^{-1}$ 1720 (ester, aldehyde), 1675 (conjugated ketone), 1590 (double bond), 1305, 1145 (sulfone).

NMR (CDCl$_3$): Major peaks are shown below.

| δ(ppm) | | | |
|---|---|---|---|
| 9.60 | 1H | s | CHO |
| 7.82 | 2H | d | J = 8 Hz, 4″-OCOCH$_2$-C$_6$H$_4$-SO$_2$CH$_3$ |
| 7.45 | 2H | d | J = 8 Hz, 4″-OCOCH$_2$-C$_6$H$_4$-SO$_2$CH$_3$ |
| 7.23 | 1H | d | J = 16 Hz  H$_{11}$ |
| 6.18 | 1H | d | J = 16 Hz  H$_{10}$ |
| 5.85 | 1H | d | J = 10 Hz  H$_{13}$ |
| 3.78 | 2H | s | 4″-OCOCH$_2$-C$_6$H$_4$-SO$_2$CH$_3$ |
| 3.59 | 3H | s | 3″′-OCH$_3$ |
| 3.46 | 3H | s | 2″′-OCH$_3$ |
| 3.00 | 3H | s | 4″-OCOCH$_2$-C$_6$H$_4$-SO$_2$CH$_3$ |
| 2.47 | 6H | s | 3′-N(CH$_3$)$_2$ |
| 1.76 | 3H | s | 12CH$_3$ |

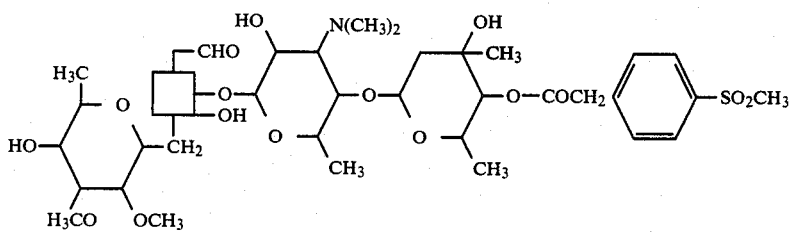

In 30 ml of methanol was dissolved 1.1 g of 2′-O-acetyl-4″′-O-chloroacetyl-4″-O-(4-methylsulfonylphenylacetyl)tylosin. The solution was stirred at 60° C. for 40 hours. After methanol was removed by distillation under reduced pressure, the residue was subjected

EXAMPLE 2

Preparation of 4''-O-(4-Methylthiophenylacetyl)tylosin

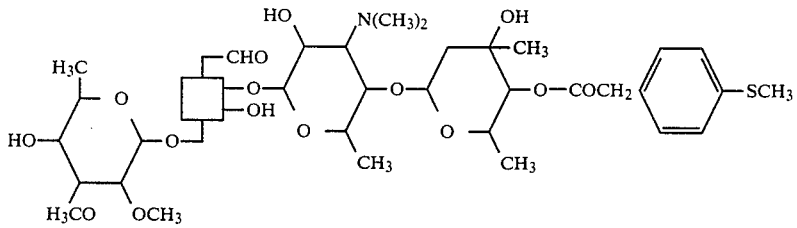

In 5 ml of ethyl acetate and 0.33 ml (2.3 mmols) of triethyl amine was dissolved 420 mg (2.3 mmols) of p-methylthiophenylacetic acid. Under cooling to −15° C., 0.29 ml (2.3 mmols) of pivalic chloride was added to the solution followed by stirring for 15 minutes. To the mixture were added 0.8 ml of pyridine and 0.8 g (0.84 mmol) of 2'-O-acetyltylosin. The mixture was stirred for 20 hours at room temperature. After the reaction solution was washed with an aqueous solution of sodium hydrogen carbonate and with an aqueous sodium chloride solution and then dried over anhydrous sodium sulfate, the solution was concentrated under reduced pressure. Toluene was added to the residue. The mixture was again concentrated under reduced pressure to remove pyridine. Thus crude powders of 2'-O-acetyl-4'',4'''-O-(4-methylthiophenylacetyl)tylosin were obtained. The powders were dissolved in 40 ml of 9% ammonia-methanol and 5 ml of water. The solution was allowed to stand for 6 hours.

After benzene was added to the solution, methanol was removed by distillation under reduced pressure. Benzene was added to the residue. After the mixture was washed with an aqueous sodium chloride solution and dried over sodium sulfate, it was concentrated under reduced pressure. The residue was subjected to precipitation from benzene-hexane to obtain crude powders of 2'-O-acetyl-4''-O-(4-methylthiophenylacetyl)tylosin. The powders were dissolved in 40 ml of methanol and the solution was stirred under reflux for 20 hours. After the reaction solution was concentrated under reduced pressure, the residue was subjected to column chromatography (developing solvent: benzene/acetone (5/1 to 3/1)). The fractions eluted out in TLC using silica gel developed with benzene/acetone (3/2) which exhibited a color with sulfuric acid at an Rf value of 0.50 were collected and concentrated under reduced pressure. The residue was washed with isopropyl ether to obtain 405 mg of the above-mentioned compound. Yield 45%.

m.p.: 105°–108° C.

[α]$_D$: −35.1° (c 1.0, CH$_3$OH).

UV: λ$_{max}$$^{CH3OH}$ 281 nm (ε 19,000), 262.5 nm (ε 19,400).

IR: ν$_{max}$ cm$^{-1}$ 1720 (ester, aldehyde), 1675 (conjugated ketone), 1590 (double bond).

NMR (CDCl$_3$) Major peaks are shown below.

| δ(ppm) | | | |
|---|---|---|---|
| 9.59 | 1H s | | CHO |
| 7.23 | 1H d | J = 16 Hz | H$_{11}$ |
| 7.16 | 4H s | | 4''-OCOCH$_2$—⟨⟩—SCH$_3$ |
| 6.19 | 1H d | J = 16 Hz | H$_{10}$ |
| 3.62 | 2H s | | 4''-OCOCH$_2$—⟨⟩—SCH$_3$ |
| 3.58 | 3H s | | 3'''OCH$_3$ |
| 3.45 | 3H s | | 2'''OCH$_3$ |
| 2.45 | 6H s | | 3'-N(CH$_3$)$_2$ |
| 2.41 | 3H s | | 4''-OCOCH$_2$—⟨⟩—SCH$_3$ |
| 1.77 | 3H s | | 12-CH$_3$ |

EXAMPLE 3

Preparation of 4''-O-(4-O-Acetylphenylacetyl) YT 3927

(1) 2'-O-Acetyl YT 3927

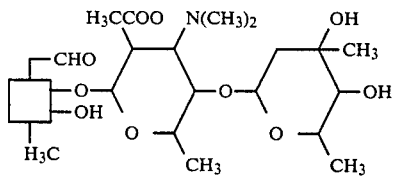

To 300 mg (0.41 mmol) of YT 3927 were added 3 ml of acetone and 0.1 ml of acetic anhydride. The mixture was stirred at room temperature overnight. Water and ammonia water were added to the reaction solution to adjust pH to 10. Thereafter, the reaction solution was extracted twice with ethyl acetate. After the extract was washed with water and dried over sodium sulfate, it was concentrated under reduced pressure. The above-mentioned compound was quantitatively obtained.

(2) 2'-O-Acetyl-4''-O-(4-acetylphenylacetyl)YT3927

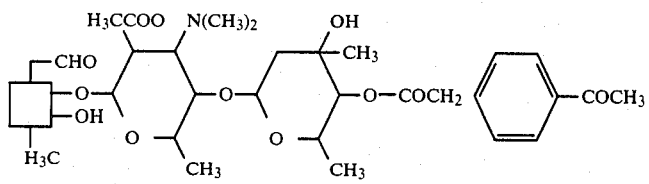

A solution of 242 mg (1.36 mmol) of p-acetylphenylacetic acid in 2.5 ml of ethyl acetate and 0.19 ml (1.36 mmol) of triethyl amine was cooled to −15° C. Under cooling, 0.17 ml (1.36 mmol) of pivalic chloride was added thereto followed by stirring for 30 minutes. To the mixture were added 0.4 ml of pyridine and 310 mg (0.41 mmol) of 2'-O-acetyl YT 3927. The resultant mixture was stirred for 2 hours under ice cooling. To the mixture were added 1 ml of methanol and an aqueous solution of sodium hydrogen carbonate followed by stirring for 30 minutes. After the organic layer was separated, it was washed with an aqueous solution of sodium chloride and then drived over anhydrous sodium sulfate followed by concentration under reduced pressure. Toluene was again added to the concentrate. The mixture was concentrated under reduced pressure to remove pyridine. The residue was subjected to column chromatography (developing solvent: benzene/acetone (8/1)) using 9 g of silica gel. Fractions eluted out in TLC using silica gel developed with benzene/acetone (3/1) which exhibited a color with sulfuric acid at an Rf value of 0.54 were collected to obtain 240 mg of the above-mentioned compound. Yield 63%.

(3) 4"-O-(4-O-Acetylphenylacetyl) YT 3927:

NMR (CDCl$_3$): Major peaks are shown below.

| δ (ppm) | |
|---|---|
| 9.60 1H s | CHO |
| 7.84 2H d J = 8Hz | 4"-OCOCH$_2$—⟨H,COCH$_3$⟩ |
| 7.34 2H d J = 8Hz | 4"-OCOCH$_2$—⟨COCH$_3$,H⟩ |
| 7.22 1H d J = 16Hz | H$_{11}$ |
| 6.19 1H d J = 16Hz | H$_{10}$ |
| 5.60 1H d J = 10Hz | H$_{13}$ |
| 4.57 1H d J = 10Hz | H$_{4''}$ |

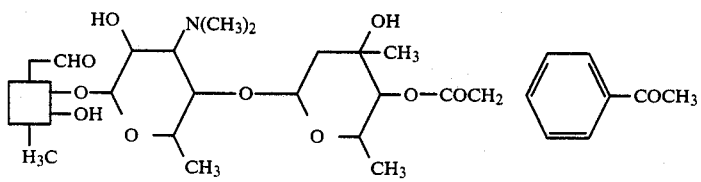

In 10 ml of methanol was dissolved 240 mg of 2'-O-acetyl-4"-O-(4-acetylphenylacetyl) YT 3927. The solution was refluxed for 20 hours. After methanol was removed by distillation under reduced pressure, the residue was subjected to column chromatography using 5 g of silica gel (developing solvent: benzene/acetone (4/1)). The fractions eluted out in TLC using silica gel developed with benzene/acetone (2/1) which exhibited a color with sulfuric acid at an Rf value of 0.49 were collected and concentrated under reduced pressure. The residual powders were washed with 2 ml of isopropyl ether to obtain 170 mg of the above-mentioned compound. Yield 74%.

m.p.: 102°–104.5° C.

[α]$_D$: −51.6° (c 1.0, CH$_3$OH).

UV: λ$_{max}^{CH3OH}$ 283.5 nm (ε 20,000), 253 nm (ε 19,000).

IR: ν$_{max}^{KBr}$ cm$^{-1}$ 1720 (ester, aldehyde), 1680 (conjugated ketone), 1595 (double bond).

| 3.73 2H s | 4"-OCOCH$_2$—⟨⟩—COCH$_3$ |
| 2.55 3H s | 4"-OCOCH$_2$—⟨⟩—COCH$_3$ |
| 2.46 6H s | 3'-N(CH$_3$)$_2$ |
| 1.76 3H s | 12-CH$_3$ |

EXAMPLE 4

Preparation of 4"-O-(4-Benzoylphenylacetyl)tylosin (1) 2'-O-Acetyl-4"-O-(4-benzoylphenylacetyl)-4"'-O-chloroacetyltylosin:

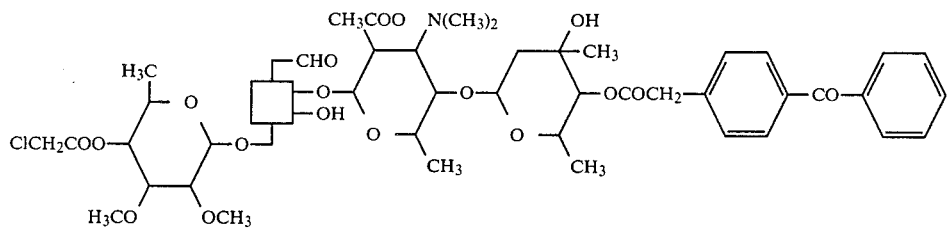

In 20 ml of ethyl acetate was dissolved 2.1 g (8.7 mmols) of p-benzoylphenylacetic acid and 1.21 ml (8.7 mmols) of triethyl amine was added to the solution. After cooling the mixture to −15° C., 1.07 ml (8.7 mmols) of pivalic chloride was dropwise added thereto followed by stirring for 20 minutes. To the mixture were added 3 ml (38 mmols) of pyridine and 3.0 g (2.9 mmols) of 2′-O-acetyl-4′′′-chloroacetyltylosin. The mixture was stirred for 2 hours under ice cooling. After completion of the reaction, 1 ml of methanol and an aqueous solution of sodium hydrogen carbonate were added and the resulting mixture was stirred for 1 hour. After the organic layer was separated, it was washed with water and then dried over anhydrous sodium sulfate. After concentrating under reduced pressure, toluene was again added to the concentrate. The mixture was concentrated under reduced pressure to remove pyridine. The residue was subjected to column chromatography (benzene/acetone (6/1)) using 200 g of silica gel. The fractions eluted out in TLC using silica gel developed with benzene/acetone (2/1) which exhibited a color with sulfuric acid at an Rf value of 0.56 were collected and concentrated under reduced pressure to obtain 3.0 g of the above-mentioned compound. Yield 82%.

NMR (CDCl$_3$): Major peaks are shown below.

| δ (ppm) | |
| --- | --- |
| 9.58 1H s | CHO |
| 7.80–7.10 10H m | 4′′-OCOCH$_2$—⌬—C(=O)—⌬ <br> H$_{11}$ |
| 6.20 1H d J = 16Hz | H$_{10}$ |
| 5.82 1H d J = 10Hz | H$_{13}$ |
| 4.03 2H s | 4′′′-OCOCH$_2$Cl |
| 3.76 2H s | 4′′-OCOCH$_2$—⌬—C(=O)—⌬ |
| 3.50 3H s | 3′′′′-OCH$_3$ |
| 3.44 3H s | 2′′′′-OCH$_3$ |
| 2.36 6H s | 3′-N(CH$_3$)$_2$ |
| 2.04 3H s | 2′-OCOCH$_3$ |

| -continued | |
| --- | --- |
| δ (ppm) | |
| 1.78 3H s | 12-CH$_3$ |

(2) 4′′-O-(4-Benzoylphenylacetyl)tylosin:

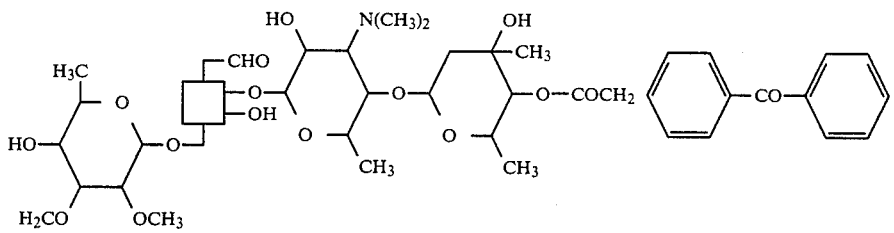

In 60 ml of methanol was dissolved 3.0 g of 2′-O-acetyl-4′′-O-(4-benzoylphenylacetyl)-4′′′-O-chloroacetyltylosin. The solution was refluxed for 34 hours. After methanol was removed by distillation under reduced pressure, the residue was subjected to column chromatography (benzene/acetone (3/1)) using 70 g of silica gel. The fractions eluted out in TLC using silica gel developed with benzene/acetone (3/2) which exhibited a color with sulfuric acid at an Rf value of 0.26 were collected and concentrated under reduced pressure. The residual solid was washed with 2 ml of isopropyl ether to obtain 1.8 g of the above-mentioned compound. Yield 66%.

m.p.: 107.5°–109.5° C.

$[\alpha]_D$: −36.2° (c 1.0, CH$_3$OH).

UV: $\lambda_{max}^{CH3OH}$ 272 nm (ε 22,000).

IR: $\nu_{max}^{KBr}$ cm$^{-1}$ 1720 (ester, aldehyde), 1670 (conjugated ketone), 1650 (benzoyl), 1590 (double bond).

NMR (CDCl$_3$): Major peaks are shown below.

| δ (ppm) | |
| --- | --- |
| 9.60 1H s | CHO |
| 7.80–7.10 10H m | 4′′-OCOCH$_2$—⌬—C(=O)—⌬ <br> H$_{11}$ |
| 6.20 1H d J = 16Hz | H$_{10}$ |
| 5.85 1H d J = 10Hz | H$_{13}$ |
| 3.77 2H s | 4′′-OCOCH$_2$—⌬—C(=O)—⌬ |
| 3.57 3H s | 3′′′′-OCH$_3$ |
| 3.46 3H s | 2′′′′-OCH$_3$ |
| 2.46 6H s | 3′-N(CH$_3$)$_2$ |
| 1.78 3H s | 12-CH$_3$ |

EXAMPLE 5

Preparation of 4''-O-(4-Methoxyphenylacetyl)tylosin (1) 2'-O-Acetyl-4'''-chloroacetyl-4''-O-(4-methoxyphenylacetyl)tylosin:

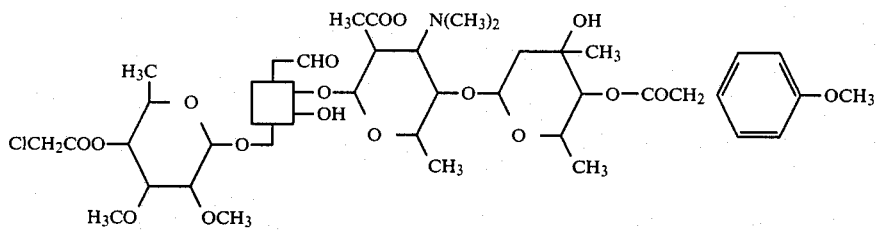

NMR (CDCl$_3$): Major peaks are shown below.

| δ (ppm) | |
|---|---|
| 9.60 1H s | CHO |
| 7.25 1H d J = 16Hz | H$_{11}$ |
| 7.15 2H d J = 9Hz | 4''-O-CO-CH$_2$-C$_6$H$_3$(H underlined ortho)-OCH$_3$ |
| 6.78 2H d J = 9Hz | 4''-O-CO-CH$_2$-C$_6$H$_3$-OCH$_3$ (H underlined meta) |
| 6.22 1H d J = 16Hz | H$_{10}$ |
| 5.85 1H d J = 10Hz | H$_{13}$ |
| 4.05 2H s | 4'''-COCH$_2$Cl |
| 3.77 3H s | 4''-O-CO-CH$_2$-C$_6$H$_4$-OC$\underline{H_3}$ |
| 3.62 2H s | 4''-O-CO-C$\underline{H_2}$-C$_6$H$_4$-OCH$_3$ |
| 3.50 3H s | 3'''-OCH$_3$ |
| 3.47 3H s | 2'''-OCH$_3$ |
| 2.35 6H s | 3'-N(Me)$_2$ |
| 2.05 3H s | 2'-OCOCH$_3$ |
| 1.75 3H s | 12-CH$_3$ |

(2) 4''-O-(4-Methoxyphenylacetyl)tylosin:

m.p.: 110°–111° C.
[α]$_D^{24}$: −43.6° (c 1.0, CH$_3$OH).
UV: λ$_{max}^{CH3OH}$ 284 nm (ε19,000), 227 nm (ε 8,700).
IR: ν$_{max}^{KBr}$ 1725 cm$^{-1}$ (ester, aldehyde), 1675 cm$^{-1}$ (conjugated ketone), 1590 cm$^{-1}$ (double bond).

NMR (CDCl$_3$): Major peaks are shown below.

| δ (ppm) | |
|---|---|
| 9.59 1H s | CHO |
| 7.25 1H d J = 16Hz | H$_{11}$ |
| 7.15 2H d J = 9Hz | 4''-O-CO-CH$_2$-C$_6$H$_3$(H underlined ortho)-OCH$_3$ |
| 6.77 2H d J = 9Hz | 4''-O-CO-CH$_2$-C$_6$H$_3$-OCH$_3$ (H underlined meta) |
| 6.18 1H d J = 16Hz | H$_{10}$ |
| 3.73 3H s | 4''-O-CO-CH$_2$-C$_6$H$_4$-OC$\underline{H_3}$ |
| 3.60 2H s | 4''-O-CO-C$\underline{H_2}$-C$_6$H$_4$-OCH$_3$ |
| 3.58 3H s | 3'''-OCH$_3$ |
| 3.44 3H s | 3''-OCH$_3$ |
| 2.46 6H s | 3'-N(CH$_3$)$_2$ |
| 1.77 3H s | 12-CH$_3$ |

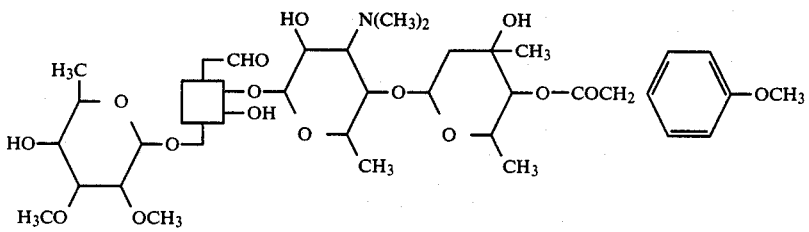

EXAMPLE 6

Preparation of 4''-O-(4-Fluorophenylacetyl)tylosin (1) 2'-O-Acetyl-4''-4'''-O-di(4-fluorophenylacetyl)-tylosin:

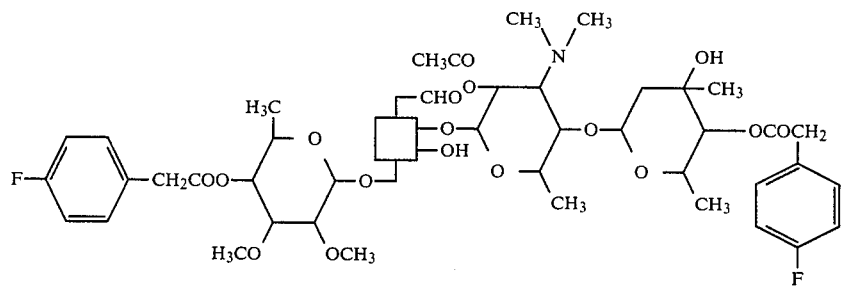

In 50 ml of methylene chloride were dissolved 5.0 g (32 mmols) of 4-fluorophenylacetic acid and 4.5 ml (32 mmols) of triethyl amine. After the solution was dissolved to −15° C., 4.0 ml (32 mmols) of pivalic chloride was dropwise added to the solution over 5 minutes followed by stirring for further 15 minutes. To the mixture were added 9 ml (110 mmols) of pyridine and 5.0 g (5.2 mmols) of 2'-O-acetyltylosin. The mixture was stirred at 5° C. for 30 hours. An aqueous solution of sodium hydrogen carbonate was added to the reaction mixture. After the organic layer was washed with an aqueous solution of sodium chloride, it was dried over anhydrous sodium sulfate. After concentrating under reduced pressure, toluene was again added and the mixture was concentrated under reduced pressure to remove pyridine. The residue was subjected to column chromatography (benzene/acetone (7/1)) using 150 g of silica gel. The fractions eluted out in TLC using silica gel developed with benzene/acetone (3/1) which exhibited a color with sulfuric acid at an Rf value of 0.47 were collected and concentrated under reduced pressure. The residue was washed with hexane to obtain 3.6 L g of the above-mentioned compound (56%).

NMR (CDCl₃): Major peaks are shown below.

| δ (ppm) | |
|---|---|
| 9.67 1H s | CHO |
| 7.50–6.85 9H m | 4'',4'''- —⟨phenyl⟩—F, $H_{11}$ |
| 6.29 1H d (J = 16.Hz) | $H_{10}$ |
| 5.90 1H d (J = 10.Hz) | $H_{13}$ |
| 3.67 2H s | 4''-COCH₂—⟨phenyl⟩—F |
| 3.61 2H s | 4'''-COCH₂—⟨phenyl⟩—F |
| 3.46 3H s | 3'''-OCH₃ |
| 3.37 3H s | 2'''-OCH₃ |
| 2.40 0H s | 3'-N(CH₃)₂ |
| 2.07 3H s | 2'-COCH₃ |
| 1.79 3H s | 12-CH₃ |

(2) 4''-O-(4-Fluorophenylacetyl)tylosin:

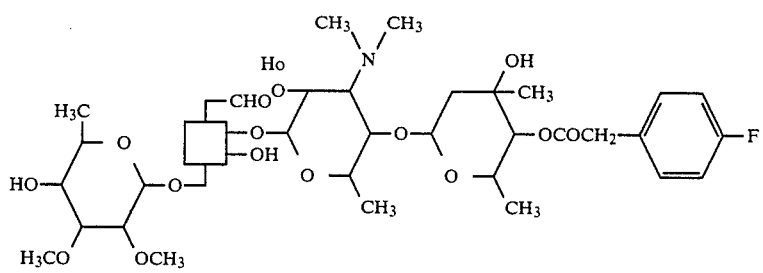

In 100 ml of methanol was dissolved 3.6 g of 2'-O-acetyl-4''-4'''-O-di(4-fluorophenylacetyl)tylosin. The solution was refluxed for 15 hours. After the reaction solution was concentrated to 40 ml, 60 ml of 17% ammonia-methanol and 8 ml of water were added under ice cooling. The mixture was stirred at 10° C. for 7 hours. After 25 ml of benzene was added, the mixture was concentrated under reduced pressure. Ethyl acetate was added to the residue. After water was separated, the system was dried over anhydrous sodium sulfate. After concentrating under reduced pressure, the residue was subjected to column chromatography (benzene/acetone (3/1)) using 130 g of silica gel. The fractions eluted out in TLC using silica gel developed with benzene/acetone (3/2) which exhibited a color with sulfuric acid at an Rf value of 0.23 were collected and concentrated under reduced pressure. The residual white powders were dissolved in 20 ml of benzene. After insoluble matters were filtered off, the filtrate was dropwise added to 150 ml of hexane to cause precipitation. Thus 1.36 g of the above-mentioned compound was obtained as white powders (44%).

m.p.: 107°–109° C.

[α]$_D$: −40.3° (c 1.0, CH$_3$OH).

UV: λ$_{max}^{CH_3OH}$ 284 nm (ε 20,000), 273 nm (sh), 267 nm (sh).

IR: ν$_{max}^{KBr}$ cm$^{-1}$ 1720 (ester, aldehyde), 1680 (conjugated ketone), 1595 (double bond).

NMR (CDCl$_3$)

| δ (ppm) | | |
|---|---|---|
| 9.69 1H s | | CHO |
| 7.45–6.85 5H m | | |

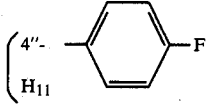

| 6.26 1H d (J = 16Hz) | H$_{10}$ |
| 5.92 1H d (J = 10Hz) | H$_{13}$ |
| 3.67 2H s | |

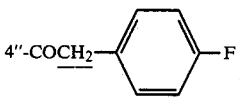

| 3.61 3H s | 3'''-OCH$_3$ |
| 3.50 3H s | 2'''-OCH$_3$ |
| 2.50 6H s | 3'-N(CH$_3$)$_2$ |
| 1.80 3H s | 12-CH$_3$ |

EXAMPLE 7

Preparation of 4''-O-(4-Fluorobenzylsulfonyl)tylosin (1) 2'-O-Acetyl-4''-O-(4-fluorobenzylsulfonyl)-4'''-O-chloroacetyltylosin:

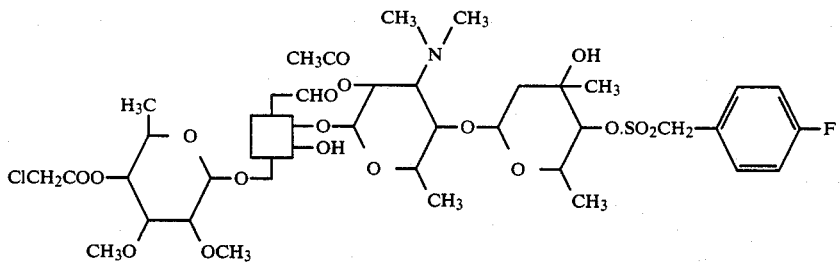

In 5 ml of methylene chloride and 2 ml of pyridine was dissolved 1.0 g (0.97 mmol) of 2'-O-acetyl-4'''-O-chloroacetyltylosin. Uncer cooling to −20° C., 350 mg (1.6 mmol) of 4-fluorobenzylsulfonyl chloride was added to the solution. The mixture was stirred for 1 hour. The reaction solution was transferred into an aqueous solution of sodium hydrogen carbonate. After the organic layer was washed with an aqueous solution of sodium chloride, it was dried over anhydrous sodium sulfate. After concentrating under reduced pressure, toluene was again added and the mixture was concentrated under reduced pressure to remove pyridine. The residue was subjected to column chromatography (benzene/acetone (6/1)) using 30 g of silica gel. The fractions eluted out in TLC using silica gel developed with benzene/acetone (3/1) which exhibited a color with sulfuric acid at an Rf value of 0.48 were collected and concentrated under reduced pressure to obtain 1.0 g of the above-mentioned compound as white powders (83%).

(2) 4''-O-(4-Fluorobenzylsulfonyl)tylosin:

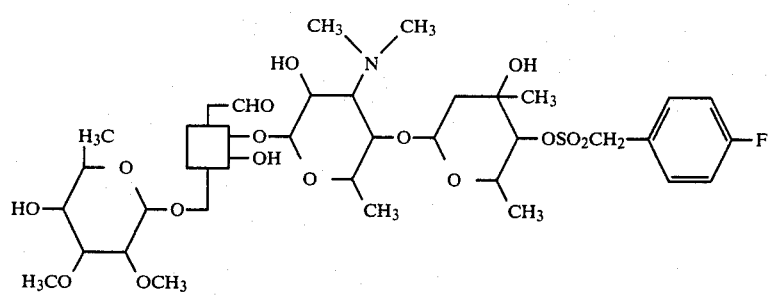

In 20 ml of methanol was dissolved 1.0 g of 2'-O-acetyl-4''-O-(4-fluorobenzylsulfonyl)tylosin. The solution was refluxed for 24 hours. After the reaction solution was concentrated under reduced pressure, the concentrate was subjected to column chromatography (benzene/acetone (3/1) using 30 g of silica gel. The fractions eluted out in TLC using silica gel developed with benzene/acetone (2/1) which exhibited a color with sulfuric acid at an Rf value of 0.29 were collected and reprecipitated from benzene-hexane to obtain 492 mg of the above-mentioned compound (55%).

m.p.: 122°–124° C.

[α]$_D$: −27.5° (c 1.0, CH$_3$OH)

UV: λ$_{max}^{CH_3OH}$ 283 nm (ε13,000), 271 nm (sh), 265 nm (sh).

IR: ν$_{max}^{KBr}$ cm$-1$ 1720 (ester, aldehyde), 1680 (conjugated ketone), 1595 (double bond).

NMR (CDCl$_3$)

| δ(ppm) | | |
|---|---|---|
| 9.69 1H s | | CHO |
| 7.45 2H dd | J=5Hz J=9Hz | 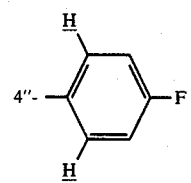 |

-continued

| δ(ppm) | | | | |
|---|---|---|---|---|
| 7.04 | 2H | t | J=9Hz | 4''- with phenyl ring, F substituent (H positions shown) |
| 7.32 | 1H | d | J=16Hz | H$_{11}$ |
| 6.25 | 1H | d | J=16Hz | H$_{10}$ |
| 5.09 | 1H | d | J=10Hz | H$_{13}$ |
| 4.41 | 2H | s | | 4''-SO$_2$CH$_2$–C$_6$H$_4$–F |
| 3.62 | 3H | s | | 3'''OCH$_3$ |
| 3.50 | 3H | s | | 2'''OCH$_3$ |
| 2.49 | 6H | s | | 3'-N(CH$_3$)$_2$ |
| 1.80 | 3H | s | | 12-CH$_3$ |

EXAMPLE 8

Preparation of 4''-O-(4-Acetylphenylacetyl)tylosin (1) 2'-O-Acetyl-4''-O-(4-acetylphenylacetyl)-4'''-O-chloroacetyltylosine:

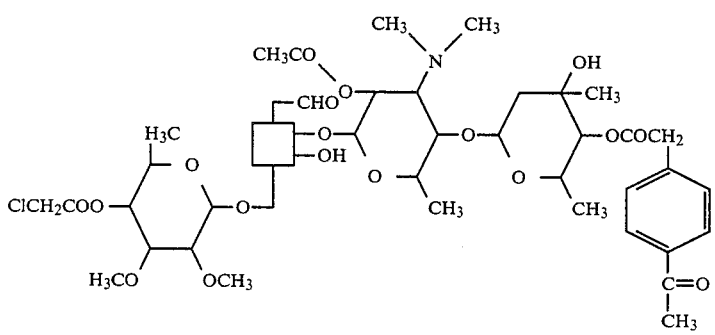

In 7 ml of methylene chloride and 0.38 ml of triethyl amine was dissolved 484 mg (2.7 mmols) of 4-acetylphenylacetic acid. Under cooling to −15° C., 0.33 ml (2.7 mmols) of pivalic chloride was dropwise added. After stirring for 15 minutes, 0.8 ml (10 mmols) of pyridine and 900 mg (0.87 mmol) of 2'-O-acetyl-4'''-O-chloroacetyltylosin were added to the mixture. The resulting mixture was stirred at 7° C. for 3 hours. An aqueous solution of sodium hydrogen carbonate was added to the reaction solution. After the organic layer was washed with a saturated aqueous solution of sodium chloride, it was dried over anhydrous sodium sulfate. After concentrating under reduced pressure, toluene was again added and the mixture was concentrated under reduced pressure to remove pyridine. The residue was subjected to column chromatography (benzene/acetone (6/1)) using 30 g of silica gel. The fractions eluted out in TLC using silica gel developed with benzene/acetone (3/1) which exhibited a color with sulfuric acid at an Rf value of 0.30 were collected and concentrated under reduced pressure to obtain 700 mg of the above-mentioned compound as white powders (67%).

NMR (CDCl$_3$)

| δ(ppm) | | | | |
|---|---|---|---|---|
| 9.70 | 1H | s | | CHO |
| 7.92 | 2H | d | J=8Hz | 4''-phenyl-C(=O)CH$_3$ (ortho H's) |
| 7.42 | 2H | d | J=8Hz | 4''-phenyl-C(=O)CH$_3$ (meta H's) |
| 7.32 | 1H | d | J=16Hz | H$_{11}$ |
| 6.28 | 1H | d | J=16Hz | H$_{10}$ |
| 5.92 | 1H | d | J=10Hz | H$_{13}$ |
| 4.09 | 1H | s | | 4'''-COCH$_2$Cl |
| 3.78 | 2H | s | | 4''-COCH$_2$–C$_6$H$_4$–C(=O)CH$_3$ |
| 3.54 | 3H | s | | 3'''-OCH$_3$ |
| 3.50 | 3H | s | | 2'''-OCH$_3$ |
| 2.58 | 3H | s | | 4''-C$_6$H$_4$–C(=O)CH$_3$ |
| 2.40 | 6H | s | | 3'-N(CH$_3$)$_2$ |
| 1.80 | 3H | s | | 12-CH$_3$ |

(2) 4''-O-(4-Acetylphenylacetyl)tylosin:

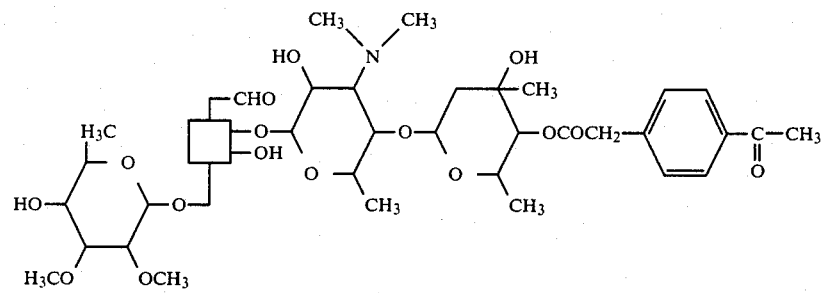

In 15 ml of methanol was dissolved 700 mg of 2'-O-acetyl-4''-O-(4-acetylphenylacetyl)-4'''-O-chloroacetyltylosin. The solution was refluxed for 10 hours. After concentrating the reaction solution, the concentrate was subjected to column chromatography (chloroform/methanol (40/1)) using 25 g of silica gel. The fractions eluted out in TLC using silica gel developed with chloroform/methanol (10/1) which exhibited a color with sulfuric acid at an Rf value of 0.46 were collected and concentrated under reduced pressure. The residual white powders were washed with isopropyl ether to obtain 380 mg of the above-mentioned compound (60%).

m.p.: 116°–119° C.

$[\alpha]_D$: −35.2° (c 1.0, $CH_3OH$).

UV: $\lambda_{max}^{CH3OH}$ 283 nm (ϵ20,000), 254 nm (ϵ18,000).

IR: $\nu_{max}^{CHCl3}$ cm$^{-1}$ 1720 (ester, aldehyde), 1680 (conjugated ketone),

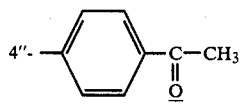

1590 (double bond).

NMR ($CDCl_3$)

| δ(ppm) | | | |
|---|---|---|---|
| 9.69 | 1H | s | CHO |
| 7.92 | 2H | d | J=8Hz |

| δ(ppm) | | | -continued |
|---|---|---|---|
| 7.43 | 2H | d | J=8Hz |
| 7.32 | 1H | d | J=16Hz | $H_{11}$
| 6.24 | 1H | d | J=16Hz | $H_{10}$
| 5.92 | 1H | d | J=10Hz | $H_{13}$
| 3.78 | 2H | s | |
| 3.61 | 3H | s | 3'''-OCH_3 |
| 3.49 | 3H | s | 2'''-OCH_3 |
| 2.58 | 3H | s | |
| 2.49 | 6H | s | 3'-N(CH_3)_2 |
| 1.80 | 3H | s | 12-CH_3 |

EXAMPLE 9

Preparation of 4''-O-(2-Fluorophenylacetyl)tylosin (1)  2'-O-acetyl-4''-O-(2-fluorophenylacetyl)-4'''-O-chloroacetyltylosin

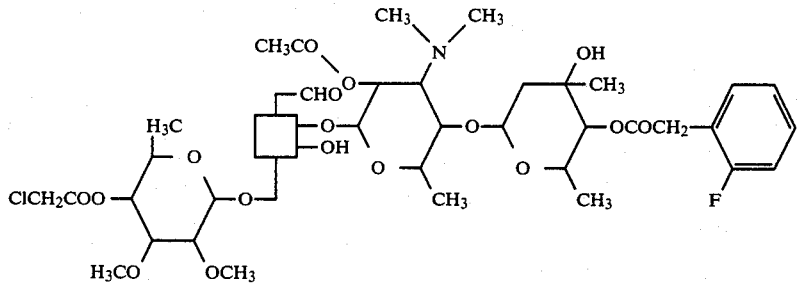

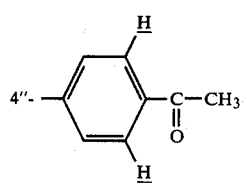

In 15 ml of methylene chloride was dissolved 1.0 g (6.5 mmols) of 2-fluorophenylacetic acid. After 0.9 ml (6.5 mmols) of triethyl amine was added to the solution, 0.8 ml (6.5 mmols) of pivalic chloride was dropwise added thereto under cooling at −15° C. After stirring for 20 minutes, 1.8 ml of pyridine and 1.0 g (0.96 mmol) of 2'-O-acetyl-4'''-O-chloroacetyltylosin were added thereto. The mixture was stirred at 10° C. for 8 hours. The reaction solution was transferred into an aqueous solution of sodium hydrogen carbonate. After the organic layer was washed with an aqueous solution of sodium chloride, it was dried over anhydrous sodium sulfate. After concentrating under reduced pressure, toluene was again added thereto and the mixture was concentrated under reduced pressure to remove pyridine. The residue was subjected to column chromatography (benzene/acetone (6/1)) using 30 g of silica gel. The fractions eluted out in TLC using silica gel developed with benzene/acetone (2/1) which exhibited a color with sulfuric acid at an Rf value of 0.59 were collected and concentrated under reduced pressure to obtain 810 mg of the above-mentioned compound (72%).

NMR (CDCl$_3$)

| δ(ppm) | | | |
|---|---|---|---|
| 9.68 | 1H | s | CHO |
| 7.45–6.90 | 5H | m | (4''- fluorophenyl, H$_{11}$) |
| 6.28 | 1H | d | J=16Hz | H$_{10}$ |
| 5.90 | 1H | d | J=10Hz | H$_{13}$ |
| 4.08 | 2H | s | 4'''-COCH$_2$Cl |
| 3.76 | 2H | s | 4''-COCH$_2$-(2-fluorophenyl) |
| 3.53 | 3H | s | 3'''-OCH$_3$ |
| 3.50 | 3H | s | 2'''-OCH$_3$ |
| 2.40 | 6H | s | 3'-N(CH$_3$)$_2$ |
| 2.80 | 3H | s | 2'-COCH$_3$ |
| 1.80 | 3H | s | 12-CH$_3$ |

(2) 4''-O-(2-Fluorophenylacetyl)tylosin:

After the reaction solution was concentrated under reduced pressure, the concentrate was subjected to column chromatography (benzene/acetone (2/1)) using 20 g of silica gel. Fractions eluted out by silica gel TLC developed with benzene/acetone (3/2) which exhibited a color with sulfuric acid at an Rf value of 0.27 were combined and concentrated under reduced pressure. The residue was washed with isopropyl ether to obtain 460 mg of the above-identified compound as white powders (58%).

m.p.: 118°–120° C.

[α]$_D^{24}$: −44.3° (c 1.0, CH$_3$OH).

UV: λ$_{max}^{CH3OH}$ 283.5 nm (ε21,000), 270 (sh), 264 (sh).

IR: ν$_{max}^{KBr}$ cm$^{-1}$ 1720 (ester, aldehyde), 1675 (conjugated ketone), 1585 (double bond).

NMR (CDCl$_3$)

| δ(ppm) | | | |
|---|---|---|---|
| 9.68 | 1H | s | CHO |
| 7.45–6.90 | 5H | m | (4''- fluorophenyl, H$_{11}$) |
| 6.25 | 1H | d | J=16Hz | H$_{10}$ |
| 5.92 | 1H | d | J=10Hz | H$_{13}$ |
| 3.77 | 2H | s | 4''-COCH$_2$-(fluorophenyl) |
| 3.61 | 3H | s | 3'''-OCH$_3$ |
| 3.49 | 3H | s | 2'''-OCH$_3$ |
| 2.50 | 6H | s | 3'-N(CH$_3$)$_2$ |
| 1.80 | 3H | s | 12-CH$_3$ |

EXAMPLE 10

Preparation of 3-O-acetyl-4''-O-(4-acetylphenylacetyl)tylosin

In 20 ml of methanol was dissolved 810 mg of 2'-O-acetyl-4''-O-(fluorophenylacetyl)-4'''-O-chloroacetyl-tylosin. The solution was heated under reflux overnight.

(1) 3,2'-O-Diacetyl-4'',4'''-di-O-(4-acetylphenylacetyl)-tylosin:

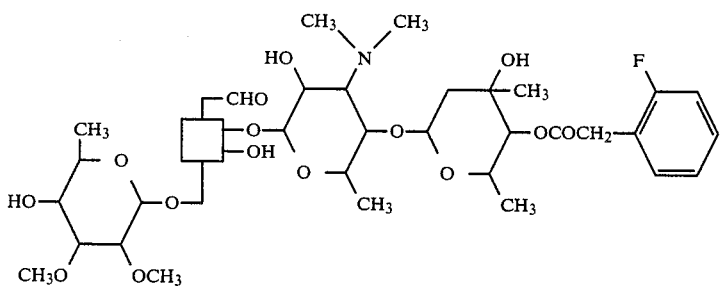

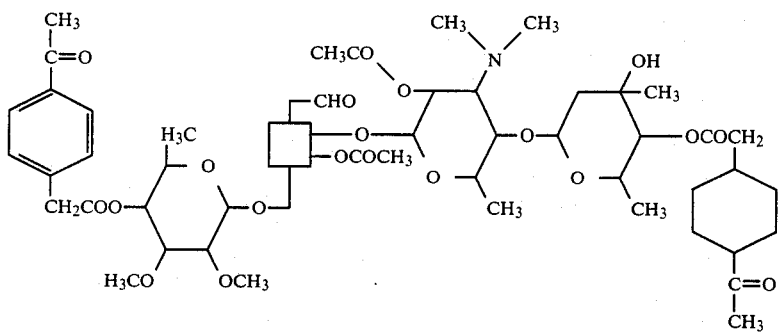

In 20 ml of methylene chloride and 1.48 ml (10.6 mmols) of triethyl amine was dissolved 1.89 g (10.6 mmols) of 4-acetylphenylacetic acid. The solution was cooled to −15° C. and 1.31 ml (10.6 mmols) of pivalic chloride was dropwise added thereto over 5 minutes. After stirring for 30 minutes, 4 ml of pyridine and 2.1 g (2.1 mmols) of 3,2′-di-O-acetyltylosin were added. The resulting mixture was stirred at room temperature for 5 hours. After the reaction solution was ice-cooled, an aqueous solution of sodium hydrogen carbonate was added and the mixture was stirred for 1 hour. After the organic layer was washed with a diluted hydrochloric acid aqueous solution (pH 2), an aqueous solution of sodium hydrogen carbonate and then an aqueous solution of sodium chloride, the organic layer was dried over anhydrous sodium sulfate followed by concentration under reduced pressure. The residue was subjected to column chromatography (developing solvent: benzene/acetone (6/1)) using 120 g of silica gel. Fractions eluted out by silica gel TLC developed with benzene/acetone (3/1) which exhibited a color with sulfuric acid at an Rf value of 0.30 were combined and concentrated under reduced pressure to obtain 2.52 g of the above-identified compound as white powders (91%).

NMR(CDCl₃): Major peaks are shown below.

| δ(ppm) | | | | |
|---|---|---|---|---|
| 9.53 | 1H | s | | CHO |
| 7.84 | 4H | d | J=8Hz | 4″,4‴- —⟨C₆H₄⟩— COCH₃ |
| 7.38 | 2H | d | J=8Hz | 4″,4‴- —⟨C₆H₄⟩— COCH₃ |
| 7.31 | 2H | d | J=8Hz | |
| 6.20 | 1H | d | J=16Hz | H₁₀ |
| 5.85 | 1H | d | J=10Hz | H₁₃ |
| 3.72 | 2H | s | | 4″-COCH₂—⟨C₆H₄⟩—COCH₃ |
| 3.67 | 2H | s | | 4‴-COCH₂—⟨C₆H₄⟩—COCH₃ |
| 3.40 | 3H | s | | 3‴-OCH₃ |
| 3.32 | 3H | s | | 2‴-OCH₃ |
| 2.54 | 6H | s | | 4″,4‴- —⟨C₆H₄⟩—COCH₃ |
| 2.34 | 6H | s | | 3′-N(CH₃)₂ |
| 2.05 | 3H | s | | 3,2′-OCOCH₃ |
| 2.03 | 3H | s | | |
| 1.78 | 3H | s | | 12-CH₃ |

(2) 3-O-acetyl-4″-O-(4-acetylphenylacetyl)tylosin:

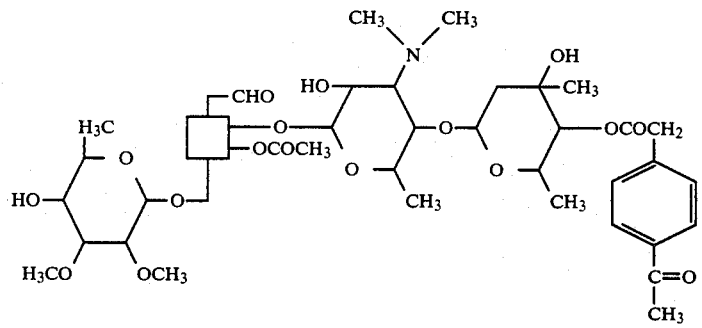

In 60 ml of methanol was dissolved 2.26 g of 3,2′-di-O-acetyl-4″,4‴-di-O-(4-acetylphenylacetyl)tylosin. The solution was refluxed for 20 hours. After the reaction solution was ice-cooled, 60 ml of 17% ammonia-methanol was added thereto. The mixture was stirred for 2.5 hours. After 20 ml of benzene was added thereto, the mixture was concentrated at low temperatures under reduced pressure. The residue was subjected to column chromatography (benzene/acetone (3/1)) using 60 g of silica gel. Fractions eluted out by silica gel TLC developed with benzene/acetone (3/2) which exhibited a color with sulfuric acid at an Rf value of 0.27 were combined and concentrated under reduced pressure. The residue was washed with isopropyl ether to obtain 680 mg of the above-identified compound as white powders (36%).

m.p.: 107°–111° C.

$[\alpha]_D$: −28.9° (c 1.0, CH$_3$OH).

UV: $\lambda_{max}^{CH3OH}$ 282.5 nm ($\epsilon$22,000), 253.5 nm ($\epsilon$20,000).

IR: $\nu_{max}^{KBr}$ cm$^{-1}$ 1730 (ester, aldehyde), 1675 (conjugated ketone), 1590 (double bond).

NMR (CDCl$_3$)

| δ(ppm) | | | | |
|---|---|---|---|---|
| 9.55 | 1H | s | | CHO |
| 7.84 | 2H | d | J=8Hz | 4″- 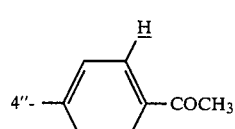 -COCH$_3$ |
| 7.34 | 2H | d | J=8Hz | 4″- 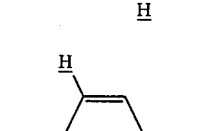 -COCH$_3$ |
| 7.32 | 1H | d | J=16Hz | H$_{11}$ |

What is claimed is:

1. A tylosin derivative represented by formula:

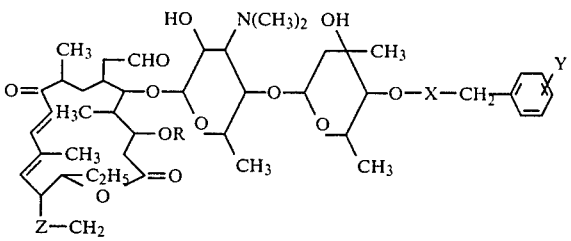

wherein R represents a hydrogen atom, an acetyl group or a propionyl group; X represents a group —CO— or —SO$_2$—; Y represents a fluorine atom, an acetyl group, a methanesulfonyl group, a methylthio group, a benzoyl group or a methoxy group bound to the benzyl group at the 2-position or 4-position; and Z represents a D-mycinose residue:

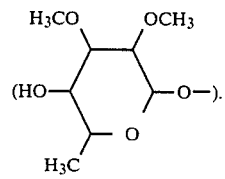

2. A tylosin derivative according to claim 1 wherein R is a hydrogen atom.

3. A tylosin derivative according to claim 2 wherein Z is a D-mycinose residue.

4. A tylosin derivative according to claim 1 or 2 wherein Y is a group bound to a benzyl group at the 4-position thereof.

* * * * *